United States Patent
Leblanc-Bazinet et al.

(10) Patent No.: US 12,125,578 B2
(45) Date of Patent: *Oct. 22, 2024

(54) SYSTEMS AND METHODS FOR GENERATING PERSONALIZED NUTRITION PRESCRIPTIONS AND MODIFYING THE PERSONALIZED NUTRITION PRESCRIPTIONS BASED ON FEEDBACK

(71) Applicant: DSS Sports Group Inc., Largo, FL (US)

(72) Inventors: Camille Leblanc-Bazinet, Largo, FL (US); David A. Lipson, Largo, FL (US)

(73) Assignee: DSS Sports Group Inc., Largo, FL (US)

( * ) Notice: Subject to any disclaimer, the term of this patent is extended or adjusted under 35 U.S.C. 154(b) by 5 days.

This patent is subject to a terminal disclaimer.

(21) Appl. No.: 18/162,213

(22) Filed: Jan. 31, 2023

(65) Prior Publication Data
US 2023/0402153 A1 Dec. 14, 2023

Related U.S. Application Data

(63) Continuation of application No. 17/835,948, filed on Jun. 8, 2022, now Pat. No. 11,581,085.

(51) Int. Cl.
*G16H 20/60* (2018.01)
(52) U.S. Cl.
CPC .................................. *G16H 20/60* (2018.01)
(58) Field of Classification Search
CPC ......... G16H 20/10; G16H 20/60; G16H 80/00

(Continued)

(56) References Cited

U.S. PATENT DOCUMENTS

| 4,951,197 A | 8/1990 | Mellinger | |
|---|---|---|---|
| 2011/0218407 A1* | 9/2011 | Haberman | G16H 50/20 600/300 |

(Continued)

FOREIGN PATENT DOCUMENTS

| JP | 2017221752 A | * 12/2017 | ................ B65B 1/16 |
|---|---|---|---|
| WO | WO-2018234083 A1 | * 12/2018 | ............. G16H 20/60 |

OTHER PUBLICATIONS

Tumnark, Piyaporn; Ontology-Based Personalized Performance Evaluation and Dietary Recommendation for Weightlifting; Universidade do Porto (Portugal). ProQuest Dissertations Publishing, 2018. 27720368 (Year: 2018) (248 pages).

*Primary Examiner* — Hiep V Nguyen
(74) *Attorney, Agent, or Firm* — Esplin & Associates, PC

(57) ABSTRACT

System and method for generating personalized nutrition prescriptions and modifying the personalized nutrition prescriptions based on feedback. Exemplary implementations may: receive user input defining biometric information, physique goals associated with individual users, and/or other information; provide the nutrition prescriptions to the individual users based on the biometric information and the physique goals; provide the nutrition prescriptions to the individual users; obtain feedback from the individual users; modify the nutrition prescriptions based on comparison between the obtained feedback and projected progress towards the physique goals associated with the individual users; provide the modified nutrition prescriptions to the individual users; and/or other exemplary implementations.

20 Claims, 5 Drawing Sheets

(58) Field of Classification Search
USPC .............................................................. 705/2
See application file for complete search history.

(56) References Cited

U.S. PATENT DOCUMENTS

| | | | |
|---|---|---|---|
| 2016/0349104 A1* | 12/2016 | Yuen .................... | A61B 5/7275 |
| 2017/0116879 A1 | 4/2017 | Baarman | |
| 2017/0323582 A1* | 11/2017 | Nusbaum ............... | G16H 20/60 |
| 2019/0244541 A1 | 8/2019 | Hadad | |

* cited by examiner

SYSTEMS AND METHODS FOR GENERATING PERSONALIZED NUTRITION PRESCRIPTIONS AND MODIFYING THE PERSONALIZED NUTRITION PRESCRIPTIONS BASED ON FEEDBACK

FIELD OF THE DISCLOSURE

The present disclosure relates to systems and methods for generating personalized nutrition prescriptions and modifying the personalized nutrition prescriptions based on feedback.

BACKGROUND

Methods for providing diets or nutrition recommendations are known. Diets and/or nutrition recommendations may include personalized elements based on user input related to the user's body composition and/or other information. Diets and/or nutrition recommendations may provide users with calorie limits, serving sizes, types of foods to be consumed, and/or other nutritional information.

SUMMARY

General diets provided to many different individuals may not always result in the desired result for each individual. Individuals having different ages, genders, lifestyles, and/or body compositions may require different nutritional recommendations, dietary regiments, fitness plans, etc., to achieve their desired goals. As such, personalized nutrition prescriptions tailored to an individual's body composition, lifestyle, physical appearance, and/or other information may be preferable in achieving results. Individualized/personalized nutrition prescriptions may provide individuals with nutrition recommendations to be consumed that are optimized for the individual users' bodies. However, bodily changes, adherence to the nutrition prescription, and/or other factors may impact the efficacy of the prescriptions over time. One or more aspects presented in the disclosure aim to propose solutions to modify personalized nutrition prescriptions to compensate for (i.e., remedy) factors that may cause the prescriptions to lose efficacy. The modifications may be based on feedback from the individual(s) and/or other information. Modifications based on an individual's bodily response to the prescription, compliance with the prescription, and/or other information may be used to optimize results for the individual.

One or more aspects of the present disclosure include a system for generating personalized nutrition prescriptions and modifying the personalized nutrition prescriptions based on feedback. The system may include electronic storage, one or more hardware processors configured by machine-readable instructions and/or other components. Executing the machine-readable instructions may cause the one or more hardware processors to facilitate generating a personalized nutrition prescription and/or modifying the personalized nutrition prescription based on feedback from a user. The machine-readable instructions may include one or more computer program components. The one or more computer program components may include one or more of an input component, a prescription component, a feedback component, a modification component, a machine learning component, and/or other components.

The input component may be configured to receive user input defining biometric information, physique goals associated with individual users, and/or other information. The biometric information associated with the individual users may include one or more of age, gender, body fat percentage, body weight, body mass index, level of activity, and/or other information. By way of non-limiting illustration, the received user input may include first user input, and/or other inputs. The first user input may define first biometric information and a first physique goal associated with a first user.

The prescription component may be configured to determine nutrition prescriptions for the individual users. The determination may be based on the biometric information, the physique goals associated with the individual users, and/or other information. The nutrition prescriptions may specify amounts of foods within different macronutrient classifications to be consumed per a consumption period. By way of non-limiting illustration, a first nutrition prescription for the first user may be determined based on the first biometric information, the first physique goal, and/or other information. The first nutrition prescription may specify amounts of foods within different macronutrient classifications to be consumed by the first user per a first consumption period.

The prescription component may be configured to provide the nutrition prescriptions to the individual users. The individual users may be intended to consume foods in accordance with the nutrition prescription to facilitate accomplishing the physique goals associated with the individual users. By way of non-limiting illustration, the first nutrition prescription may be provided to the first user.

The feedback component may be configured to obtain feedback from the individual users. The feedback may include one or more of the individual users' body fat percentages, body weights, body mass indexes, and/or other information at or near the time that feedback is obtained. The feedback from the individual users may be compared to projected progress towards the physique goals associated with the individual users. By way of non-limiting illustration, first feedback may be obtained from the first user. The first feedback may be compared to the first user's projected progress towards the first physique goal.

The modification component may be configured to modify the nutrition prescriptions. The modification may be based on the comparison between the obtained feedback and the projected progress towards the physique goals associated with the individual users. By way of non-limiting illustration, the first nutrition prescription may be modified based on the comparison between first feedback and the projected progress by the first user towards the first physique goal.

The modification component may be configured to provide the modified nutrition prescriptions to the individual users. By way of non-limiting illustration, the modified first nutrition prescription may be provided to the first user.

These and other features, and characteristics of the present technology, as well as the methods of operation and functions of the related elements of structure and the combination of parts will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of 'a', 'an', and 'the' include plural referents unless the context clearly dictates otherwise.

DETAILED DESCRIPTION

Figure 1:
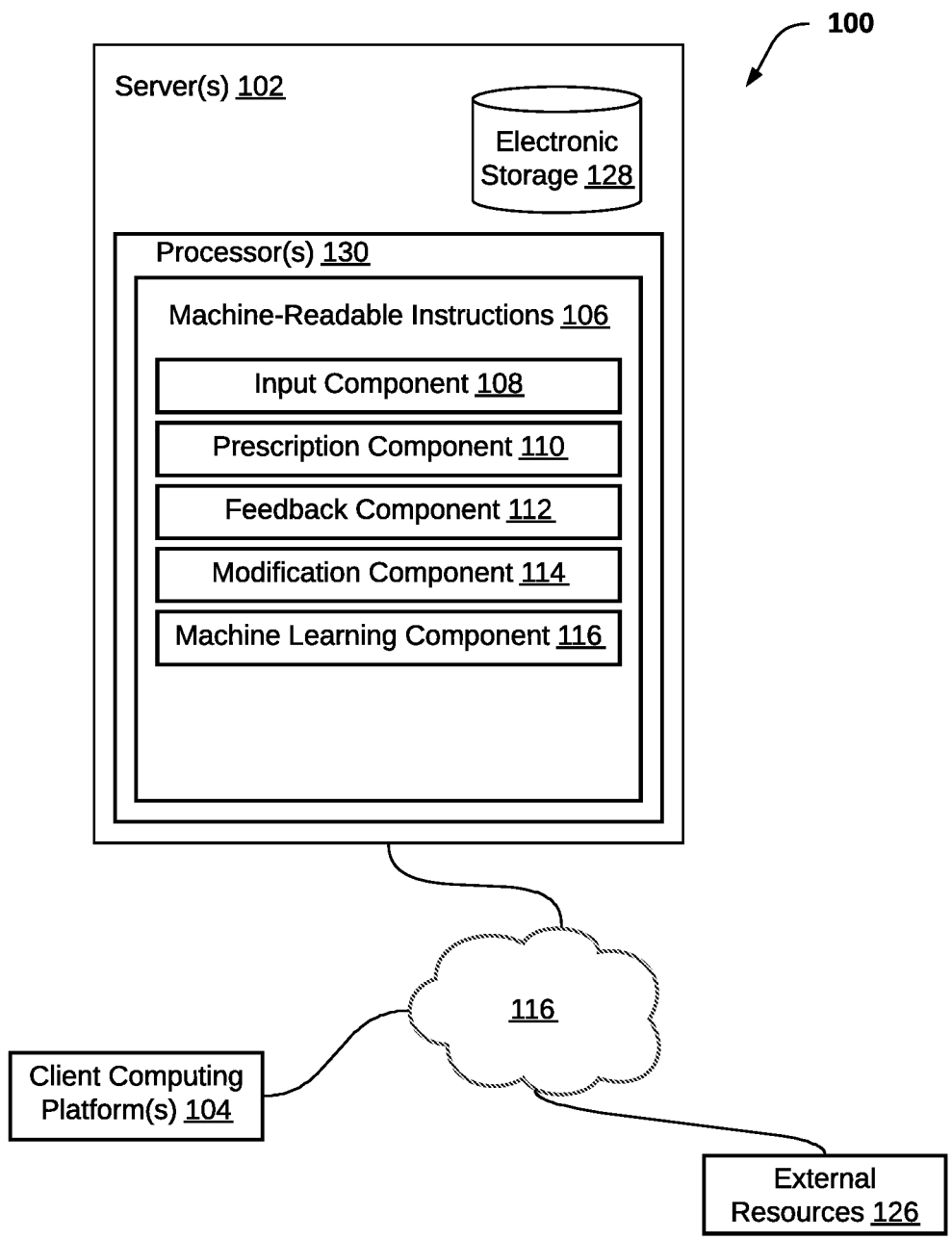
FIG. 1 illustrates a system for generating personalized nutrition prescriptions and modifying the personalized nutrition prescriptions based on feedback, in accordance with one or more implementations.

FIG. 1 illustrates a system 100 configured for generating personalized nutrition prescriptions and modifying the personalized nutrition prescriptions based on feedback, in accordance with one or more implementations. In some implementations, system 100 may include one or more servers 102. Server(s) 102 may be configured to communicate with one or more client computing platforms 104 according to a client/server architecture and/or other architectures. Client computing platform(s) 104 may be configured to communicate with other client computing platforms via server(s) 102 and/or according to a peer-to-peer architecture and/or other architectures. Users may access system 100 via client computing platform(s) 104.

Server(s) 102 may be configured by machine-readable instructions 106. Machine-readable instructions 106 may include one or more instruction components. The instruction components may include computer program components. The instruction components may include one or more of input component 108, prescription component 110, feedback component 112, modification component 114, machine learning component 116, and/or other instruction components.

Input component 108 may be configured to receive user input defining biometric information, physique goals associated with individual users, and/or other information. Biometric information may refer to human characteristics related to the individual users' body composition, physical appearance, and/or other characteristics. User input defining biometric information may reflect the user's body composition, physical appearance, and/or other characteristics at or near the time that user input is received. The biometric information associated with the individual users may include one or more of age, gender, body fat percentage, body weight, body mass index, level of activity, and/or other information. In some implementations, input component 108 may calculate the user's body mass index based on the user's weight, height, and/or other biometric information. The user input may specify numerical ranges for body fat percentage, body weight, level of activity, and/or other biometric information. For example, user input may specify a user's weight is between 150-155 pounds, and/or other ranges. In some implementations, biometric information may be obtained from external resources 126, via network(s) 116, and/or other components of system 100. For example, biometric information may be obtained from a body scanner, and/or other applications and/or other machines. By way of non-limiting illustration, the received user input may include first user input, and/or other inputs. The first user input may define first biometric information and a first physique goal associated with a first user.

User input may identify one or more physique goals associated with the individual users. The physique goals may define a desired body composition and/or physical appearance to be achieved by the individual users. In some implementations, the physique goals may include one or more of losing body weight, losing body fat, maintaining body weight, gaining muscle mass, and/or other types of goals. Multiple physique goals may be presented to the individual users via one or more user interfaces of client computing platform(s) 104. Individual user interfaces may include one or more user interface elements that represent the multiple physique goals. The one or more user interface elements may be capable of being selected to identify one or more physique goals to be achieved (i.e., accomplished) by the individual users. In some implementations, users may select a combination of one or more physique goals. For example, a user may select a first physique goal and a second physique goal to be achieved. The first physique goal may include losing body fat and the second physique goal may include gaining muscle mass.

In some implementations, input component 108 may be configured to receive user input defining numerical values and/or levels of intensity corresponding to the physique goals associated with the individual users. Individual numerical values may be one or more of a value of pounds to lose or gain, a percentage of body fat to lose, a percentage of muscle mass to gain, and/or other values. Numerical values may represent pounds, kilos, stones, and/or other units of weight corresponding to the physique goals. In some implementations, the numerical values may be included in the physique goals associated with the individual users. For example, a physique goal may be losing 15 pounds, gaining 15 pounds, and/or other goals. Individual levels of intensity may be one or more of low intensity, moderate intensity, high intensity of achieving the physique goal, and/or other levels of intensity corresponding to the physique goals. The individual levels of intensity may indicate the difficulty of accomplishing the physique goals. For example, a low intensity physique goal may be easier to achieve than a high intensity physique goal. Individual levels of intensity may be associated with individual numerical values and/or other types of values. By way of non-limiting illustration, a low level of intensity for losing body weight may correspond to 5 pounds, a moderate level of intensity for losing body weight may correspond to 10 pounds, a high level of intensity for losing body weight may correspond to 20 pounds, and/or other correspondences.

In some implementations, input component 108 may be configured to receive user input defining periods of time corresponding to the individual physique goals. An individual periods of time for an individual physique goal may specify an expected (i.e., intended) date of achievement of the physique goal. For example, an individual physique goal corresponding to a period of 2 months may be intended to be accomplished within 2 months of the physique goal being selected by a user and/or the user receiving a personalized nutrition prescription. In some implementations, the periods of time may be associated with levels of intensity and/or other information. For example, a low level of intensity for a physique goal may be associated with a period of time that is longer than a moderate level of intensity for the same physique goal. In other words, physique goals corresponding to relatively higher levels of intensity may be expected to be accomplished in a shorter period of time compared to physique goals corresponding to relatively lower levels of intensity. The periods of time may include 1 month, 3, months, 6 months, 1 year, and/or other periods of time. By way of non-limiting illustration, received user input may include a first period of time corresponding to the first physique goal. The first physique goal may be intended to be accomplished by the first user within the first period of time.

In some implementations, input component 108 may be configured to provide suggested physique goals to the individual users based on the biometric information associated with the individual users. The suggested physique goals may include correspond periods of time, levels of intensity, numerical values, and/or other information. The suggested physique goals may be determined based on one or more models of healthy body compositions according to one or more of age, gender, height, body type, and/or other information. For example, a physique goal specifying a target body weight may be suggested to a user based on biometric information including the user's age, gender, height, body type, current body weight, and/or other information. The physique goal specifying the target body weight may be determined based on the one or more models. For example, the target body weight may be associated with the healthy body weight for the user's age, gender, height, body type, and/or other information. The one or more models of healthy body composition may be stored in electronic storage 128 and/or obtained from external resources 126.

Prescription component 110 may be configured to determine nutrition prescriptions for the individual users. The determination may be based on the biometric information, the physique goals associated with the individual users, and/or other information. The nutrition prescriptions may be based on numeric values, levels of intensity, period of time, and/or other information corresponding to the physique goals. For example, users selecting the same physique goal and/or having different biometric information may be provided different nutrition prescriptions based on the individual biometric information for each user. The nutrition prescriptions may be determined to facilitate the individual users accomplishing the physique goals associated with the individual users (i.e., selected by the individual user). In other words, consumption of food in accordance with the nutrition prescriptions may facilitate the individual users achieving the individual physique goals. The nutrition prescriptions may specify amounts of foods within different macronutrient classifications to be consumed per a consumption period by the individual users. The nutrition prescriptions may include a total caloric intake amounts per a consumption period by the individual users. The total caloric intake amount may be in accordance with the amounts of food within different macronutrient classifications and/or represent the number of calories to be consumed by an individual user per a consumption period. For example, the total caloric intake amount included in a nutrition prescription may be 2000 calories per day, 1800 calories per day, and/or other rates of caloric intake. By way of non-limiting illustration, a first nutrition prescription for the first user may be determined based on the first biometric information, the first physique goal, the first period of time, and/or other information. The first nutrition prescription may specify amounts of foods within different macronutrient classifications to be consumed by the first user per a first consumption period.

In some implementations, individual macronutrient classifications may include one or more of protein, fat, carbohydrate, and/or other types of classifications. Food items may be classified under one or more of the individual macronutrient classifications. For example, 1 serving of pasta may be classified as 43.2 grams of carbohydrates and/or 1.3 grams of fat. In some implementations, the nutrition prescriptions may include food recommendations based on the specified amounts of foods within different macronutrient classifications. By way of non-limiting illustration, the food recommendations may be based on a ratio between the specified amounts of foods within the different macronutrient classifications. A nutrition prescription may specify a 3:1:1 ratio between protein, carbohydrates, and fats, respectively. The nutrition prescription may include recommendations of food having a similar ratio between protein, carbohydrate, and fat composition based on the 3:1:1 ratio. The nutrition prescription may include recommendations of food having a relatively higher protein composition based on the 3:1:1 ratio. Amounts of food may be specified using grams, milligrams, liters, and/or other units of measurement. The consumption period for the nutrition prescriptions may be 1 day, 2 days, 1 week, and/or other durations of time. The consumption period for the nutrition prescription may determine the rates of consumption for individual macronutrient classifications. For example, the rate of consumption for an individual amount of food within a macronutrient classification may be 50 grams per day, 150 grams per every 2 days, and/or other values.

In some implementations, the nutrition prescriptions may specify amounts of foods within different macronutrient classifications to be consumed for different intervals of time. The intervals of time may be one day, one week, one month, and/or other durations of time. By way of non-limiting illustration, the nutrition prescription may include amounts of foods to be consumed on a first day and/or amounts of foods to be consumed on a second day following the first day. The amounts of foods for the first day may be different than the amounts of food for the second day. In some implementations, the different amounts of foods within different macronutrient classifications for different intervals may be based on the individual user's biometric information, physique goal(s), and/or other information.

Prescription component 110 may be configured to provide the nutrition prescriptions to the individual users. By way of non-limiting illustration, the first nutrition prescription may be provided to the first user. The individual users may be intended to consume foods in accordance with the nutrition prescription to facilitate accomplishing the physique goals associated with the individual users. Consuming food in accordance with the nutrition prescriptions may include consuming foods in similar or the same amounts (within the different macronutrient classifications) as specified by the nutrition prescriptions. For example, a nutrition prescription may specify a total caloric intake of 2000 calories per day. An individual user that consumes 2050 calories within a day may be considered to have consumed foods in accordance with the nutrition prescription. In some implementations, the nutrition prescriptions may include recommendations for physical activity and/or energy expenditure. By way of non-limiting illustration, the nutrition prescriptions may include a recommendation for the individual user to increase physical activity. The increase in physical activity may be indicated in time (e.g., minutes, hours, etc.), caloric expenditure (e.g., a number of calories burned during physical activity), and/or other units of measurement.

Feedback component 112 may be configured to obtain feedback from the individual users. The feedback may include one or more of the individual users' body fat percentages, body weights, body mass indexes, and/or other information at or near the time that feedback is obtained. In some implementations, feedback may include the individual users' mood, fatigue levels, and/or other information related to the individual users. In some implementations, the feedback may be obtained through a survey (i.e., questionnaire) presented to the individual users via user interfaces of client computing platform(s) 104. The feedback may include numerical values, numerical ranges, and/or other information pertaining to the individual users' biometric information at or near the time that feedback is obtained. In some implementations, feedback may be obtained at regular intervals. By way of non-limiting illustration, feedback may be obtained from the individual users every week, 2 weeks, 10 days, and/or other intervals of time. The intervals at which feedback is obtained may be based on the periods of time corresponding to the physique goals, the individual users' biometric information, user entry identifying intervals of time for obtaining feedback, and/or other information.

The feedback from the individual users may be compared to projected progress towards the physique goals associated with the individual users. By way of non-limiting illustration, first feedback may be obtained from the first user. The first feedback may be compared to the first user's projected progress towards the first physique goal. Projected progress towards the physique goals may include individual values of biometric information (e.g., body weight, body mass index, body fat percentage, etc.) associated with expected changes in the individual users' body composition, physical appearance, and/or other information. The expected changes may be due to food consumption in accordance with the nutrition prescription. The projected progress may reflect the expected body composition and/or physical appearance of the individual users at or near the time at which feedback is obtained. By way of non-limiting illustration, projected progress may include an expected body weight for an individual user after 1 week of consuming foods in accordance with a nutrition prescription. Feedback may be obtained from the individual user after 1 week of consuming foods in accordance with the nutrition prescription and may include the individual user's actual body weight at or near the time feedback is obtained. In some implementations, feedback component 112 may determine one or more scores based on the comparisons between projected progress towards the physique goals and the obtained feedback. The scores may include numeric values, levels (e.g., low, moderate, high), and/or other types of values. For example, a high score may indicate an individual user making relatively good progress towards a physique goal compared to a low score that may indicate an individual user is making relatively worse progress towards a physique goal.

In some implementations, feedback may specify individual users' compliance with the nutrition prescription. Individual users' compliance with the nutrition prescriptions may include information regarding the individual users' actual consumption of food per the consumption periods. For example, feedback may specify amounts of foods within the different macronutrient classifications consumed by a user for individual ones of the consumption periods. In some implementations, the amounts of foods consumed by the user may be compared to the amounts of foods (within the different macronutrient classifications) specified by the nutrition prescriptions in order to determine a level of compliance between amounts of foods consumed by a user and amounts of food specified by the nutrition prescription. By way of non-limiting illustration, a low level of compliance may indicate a user consumed amounts of foods that were relatively different from the amounts of foods specified by the nutrition prescription. In some implementations, individual levels of compliance may be determined for individual macronutrient classifications of the amounts of foods consumed by the individual users. By way of non-limiting illustration, levels of compliance may be determined for individual ones of amounts of protein, carbohydrates, and fats were consumed by the user. The level of compliance for the amount of protein consumed may be based on a comparison between the amount of protein consumed and the amount of protein specified in the nutrition prescription. The level of compliance for amount of carbohydrates consumed may be based on a comparison between the amount of carbohydrates consumed and the amount of carbohydrates specified in the nutrition prescription. The level of compliance for amount of fat consumed may be based on a comparison between the amount of fat consumed and the amount of fat specified in the nutrition prescription. In some implementations, a total level of compliance with the nutrition prescription may be determined by aggregating (e.g., averaging) the individual levels of compliance for the individual different macronutrient classifications specified within the nutrition prescription.

Modification component 114 may be configured to modify the nutrition prescriptions. The modification may be based on the comparison between the obtained feedback and the projected progress towards the physique goals associated with the individual users, the physique goals, biometric information, and/or other information. Projected progress may be determined for an individual user consuming food in accordance with a nutrition prescription to achieve an individual physique goal. The projected progress may specify the expected changes to the individual user's body composition and/or physical appearance as the user consumes foods in accordance with the nutrition prescription. For example, projected progress may specify a first body weight expected after one week of consuming foods in accordance with the nutrition prescription, a second body weight expected after two weeks of consuming foods in accordance with the nutrition prescriptions, and so on and so forth until the physique goal is expected to be achieved by the user. By way of non-limiting illustration, the first nutrition prescription may be modified based on the comparison between first feedback and the projected progress by the first user towards the first physique goal. The modified first nutrition prescription may be intended to maintain the first user's progress towards accomplishing the first physique goal.

In some implementations, modifications to the nutrition prescriptions may be intended to facilitate individual users achieving the physique goals within the periods of time corresponding with the physique goals. For example, a physique goal associated with an individual user may include losing 10 pounds in two months. Feedback obtained after one month of consuming foods in accordance with a nutrition prescription based on the physique goal may indicate the individual user has lost 3 pounds. The nutrition prescription may be modified for the individual user to lose 7 pounds in one month in order to facilitate the individual user achieving the physique goal. Modifications to the nutrition prescriptions may be based on one or more of the scores, the levels of compliance, and/or other information related to obtained feedback. By way of non-limiting illustration, feedback having a high score (i.e., relatively high similarity with the projected progress) may lead to fewer modifications to a nutrition prescription compared to feedback having a low score (i.e., relatively low similarity with the projected progress). Modifications to the nutrition prescription may include modifications to the total caloric intake, the individual amounts of foods within the different macronutrient classifications to consume, the consumption period, and/or other information related to the nutrition prescription. For example, modifications to nutrition prescriptions may include increasing/decreasing the total caloric intake, increasing/decreasing the amounts of foods within the different macronutrient classifications, and/or other types of modifications to the nutrition prescriptions.

In some implementations, the modifications to the nutrition prescriptions may be made at regular intervals and/or subsequent to feedback being obtained. The regular intervals may be every 3 days, every week, every 2 weeks, and/or other intervals of time. The modifications to the nutrition prescriptions may be based on the most recent feedback obtained and/or feedback that was obtained at a prior time. For example, modifications may be based on feedback obtained at or near the time of modification, feedback obtained 1 week prior to the modifications, feedback obtained 2 weeks prior to the modifications, feedback obtained 3 weeks prior to the modifications, and/or other feedback. Modification component 114 may be configured to provide the modified nutrition prescriptions to the individual users. By way of non-limiting illustration, the modified first nutrition prescription may be provided to the first user.

In some implementations, the nutrition prescriptions, obtained feedback, the modified nutrition prescriptions may be provided as training inputs to train a machine learning model. Machine learning component 116 may be configured to train the machine learning model to modify nutrition prescriptions based on obtained feedback. In some implementations, the trained machine learning model may be stored in electronic storage 128. The trained machine learning model may accept a given nutrition prescription, given feedback associated with the given nutrition prescription, and/or other information as input to the machine learning model. The trained machine learning model may be configured to output a modified given nutrition prescription based on the input to the machine learning model. In some implementations, the machine learning model may utilize one or more of an artificial neural network, naïve bayes classifier algorithm, k means clustering algorithm, support vector machine algorithm, linear regression, logistic regression, decision trees, random forest, nearest neighbors, and/or other approaches. The machine learning component 116 may utilize training techniques such as deep learning. The machine learning component 116 may utilize training techniques such as one or more of supervised learning, semi-supervised learning, unsupervised learning, reinforcement learning, and/or other techniques.

Figure 3:
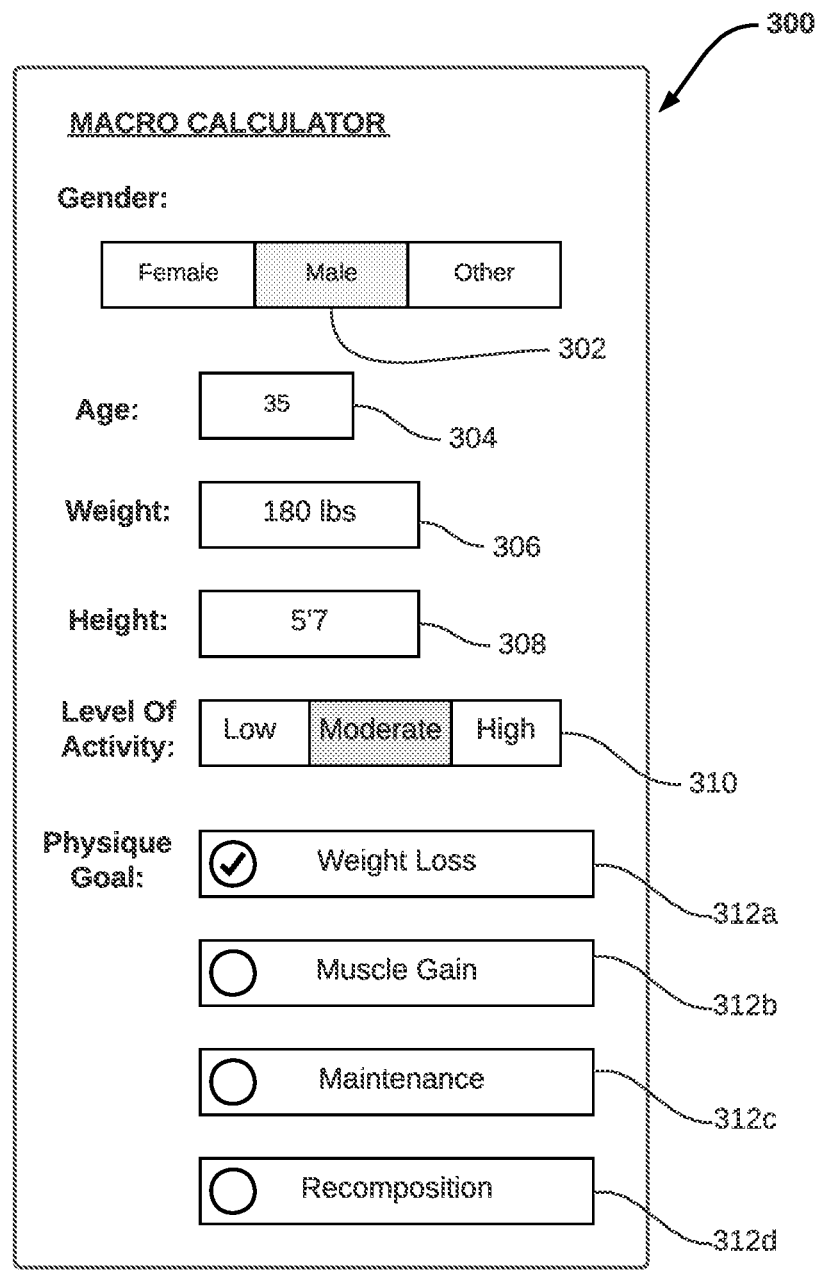
FIG. 3 illustrates a user interface of the system configured for generating personalized nutrition prescriptions and modifying the personalized nutrition prescriptions based on feedback, in accordance with one or more implementations.

FIG. 3 illustrates an exemplary user interface 300 that may be used by a system for generating personalized nutrition prescriptions and modifying the nutrition prescriptions based on feedback. User interface 300 may include one or more user interface elements and/or other components. The user interface elements may include a first input field 302, a second input field 304, a third input field 306, a fourth input field 308, a fifth input field 310, a sixth input field(s) 312a-d, and/or other user interface elements. Individual ones of the user interface elements may be capable of facilitating user selection and/or entry of biometric information, physique goals, and/or other information associated with a user. The first input field 302 may be capable of receiving user entry identifying a gender associated with the user. The second input field 304 may be capable of receiving user entry identifying an age associated with the user. The third input field 306 may be capable of receiving user entry identifying a weight associated with the user. The fourth input field 308 may be capable of receiving user entry identifying a height associated with the user. The fifth input field 310 may be capable of receiving user entry identifying a level of activity associated with the user. The sixth input field(s) 312a-d may be capable of receiving user entry identifying one or more physique goals to be achieved by the user. Individual ones of the sixth input fields 312a-d may correspond to individual physique goals that are capable of being selected by the user. Biometric information and/or physique goals specified (i.e., identified) via user interface 300 may be used to a nutrition prescription for the user.

Figure 4:
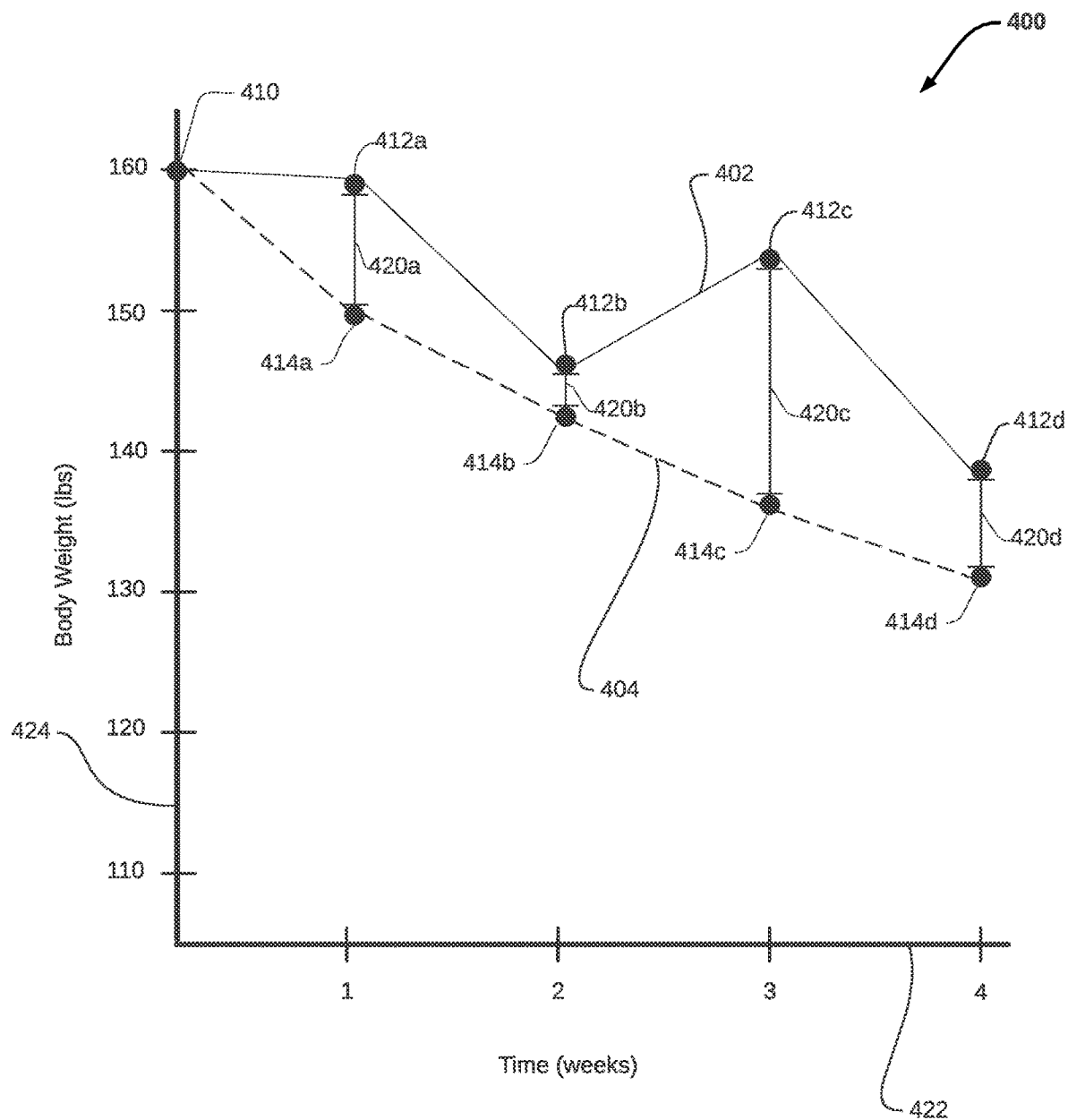
FIG. 4 illustrates an exemplary implementation of the system configured for generating personalized nutrition prescriptions and modifying the personalized nutrition prescriptions based on feedback, in accordance with one or more implementations.

FIG. 4 may illustrate an exemplary implementation of a graph 400 comparing obtained feedback and projected progress, which may be used by a system for generating personalized nutrition prescriptions and modifying the nutrition prescriptions based on feedback. Graph 400 may include a first line 402, a second line 404, a first axis 422, a second axis 424, and/or other components. First axis 422 may represent intervals of time. The intervals of time may be measures in weeks and/or other units of time. Second axis 424 may represent body weight. The body weight may be measured in pounds and/or other units of weight. First line 402 may represent a user's actual body weight over time while consuming foods in accordance with a nutrition prescription. Second line 404 may represent a user's projected body weight (i.e., projected progress) over time while consuming foods in accordance with a nutrition prescription. First line 402 may include one or more plots 412a-d representing feedback obtained from the user at different intervals of time. A first plot 412a representing the user's body weight after one week of consuming foods in accordance with the nutrition prescription, a second plot 412b representing the user's body weight after two weeks of consuming foods in accordance with the nutrition prescription, and so on and so forth. Individual plots 412a-d of first line 402 may have a corresponding plot(s) 414a-d of second line 404. Second line 404 may include one or more plots 414a-d representing projected progress for the user based on the physique goal and/or the nutrition prescription. A fifth plot 414a may represent the user's projected body weight after one week of consuming foods in accordance with the nutrition prescription, a sixth plot 414 may represent the user's projected body weight after two weeks of consuming foods in accordance with the nutrition prescription, and so on and so forth.

In some implementations, comparisons between obtained feedback and projected progress may include comparing the correspond plots between first line 402 and second line 404. Value(s) represented by first plot 412a may be compared to value(s) represented by fifth plot 414a. The comparison between first plot 412a and fifth plot 414a may be shown using first distance 420a. Value(s) represented by second plot 412b may be compared to value(s) represented by sixth plot 414b. The comparison between second plot 412b and sixth plot 414b may be shown using second distance 420b. Value(s) represented by third plot 412c may be compared to value(s) represented by seventh plot 414c. The comparison between third plot 412c and seventh plot 414c may be shown using third distance 420c. Value(s) represented by fourth plot 412d may be compared to value(s) represented by eighth plot 414d. The comparison between fourth plot 412d and eighth plot 414*d* may be shown using fourth distance 420*d*. Distances 420*a-d* may be used to determine modifications to the nutrition prescription. It should be noted that while graph 400 shows obtained feedback having values for body weight, this is not intended to be limiting. Other elements of biometric information may be compared to projected progress and/or used for modification of the nutrition prescription(s).

Figure 5B:
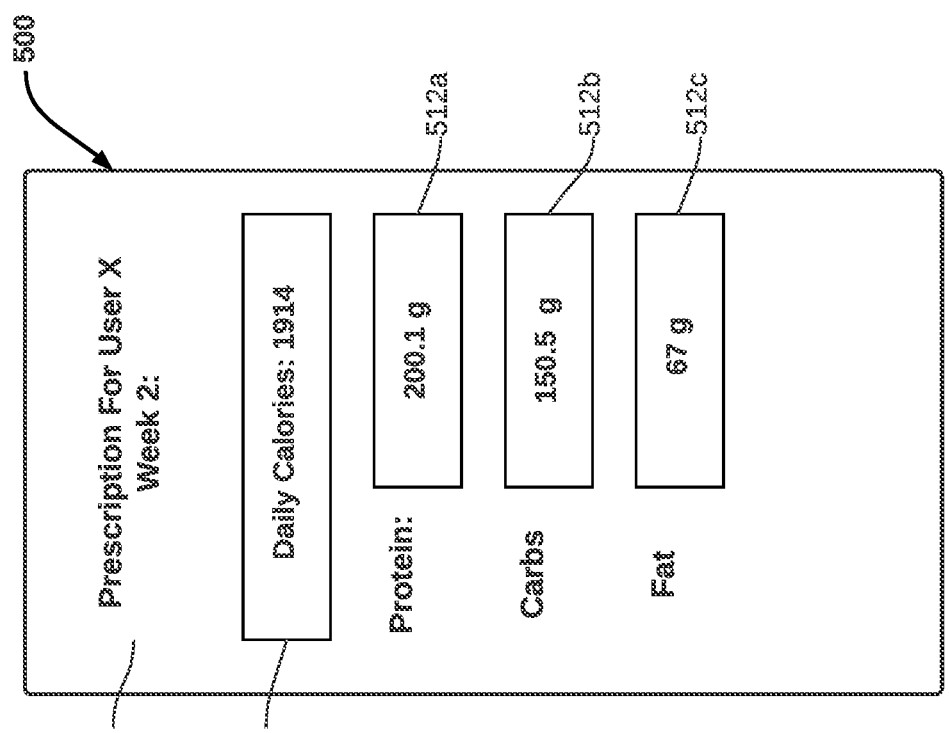
FIGS. 5A-B illustrate a user interface of the system configured for generating personalized nutrition prescriptions and modifying the personalized nutrition prescriptions based on feedback, in accordance with one or more implementations.
Figure 5A:
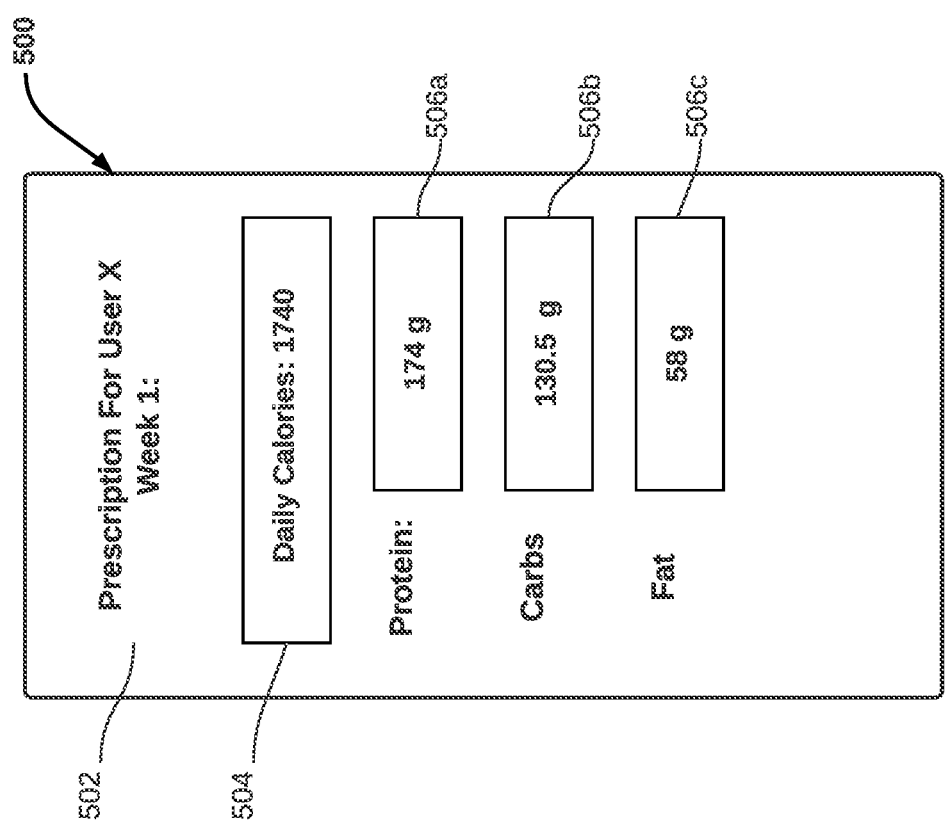

FIGS. 5A-5B illustrate an exemplary user interface 500 that may be used by a system for generating personalized nutrition prescriptions and modifying the nutrition prescriptions based on feedback. Referring to FIG. 5A, user interface 500 may present a first nutrition prescription 502 to or for a user ('USER X'). First nutrition prescription 502 may include a first total caloric intake amount 504 to be consumed by the user, one or more amounts of foods within different macronutrient classifications 506*a-c* to be consumed by the user, and/or other components. In some implementations, first nutrition prescription 502 may specify amounts of foods to be consumed for a specific interval of time. By way of non-limiting illustration, first nutrition prescription 502 may specify amounts of foods to be consumed for a week. Feedback may be obtained from the user after one week of consuming foods in accordance with first nutrition prescription 502.

Referring to FIG. 5B, user interface 500 may present a second nutrition prescription 508 to or for the user (USER X'). Second nutrition prescription 508 may include a second total caloric intake amount 510 to be consumed by the user, one or more amounts of foods within different macronutrient classifications 512*a-c* to be consumed by the user, and/or other components. In some implementations, second nutrition prescription 508 may specify amounts of foods to be consumed for a week, subsequent to the first week of consumption in accordance with the first nutrition prescription 502. In some implementations, feedback may be obtained and/or related to the user's consumption in accordance with first nutrition prescription 502. The obtained feedback may be used to determine modifications to first nutrition prescription 502. Modification to first nutrition prescription 502 may result in the generation of second nutrition prescription 508.

In some implementations, server(s) 102, client computing platform(s) 104, and/or external resources 126 may be operatively linked via one or more electronic communication links. For example, such electronic communication links may be established, at least in part, via a network such as the Internet and/or other networks. It will be appreciated that this is not intended to be limiting, and that the scope of this disclosure includes implementations in which server(s) 102, client computing platform(s) 104, and/or external resources 126 may be operatively linked via some other communication media.

A given client computing platform 104 may include one or more processors configured to execute computer program components. The computer program components may be configured to enable an expert or user associated with the given client computing platform 104 to interface with system 100 and/or external resources 126, and/or provide other functionality attributed herein to client computing platform(s) 104. By way of non-limiting example, the given client computing platform 104 may include one or more of a desktop computer, a laptop computer, a handheld computer, a tablet computing platform, a NetBook, a Smartphone, and/or other computing platforms.

External resources 126 may include sources of information outside of system 100, external entities participating with system 100, and/or other resources. In some implementations, some or all of the functionality attributed herein to external resources 126 may be provided by resources included in system 100.

Server(s) 102 may include electronic storage 126, one or more processors 130, and/or other components. Server(s) 102 may include communication lines, or ports to enable the exchange of information with a network and/or other computing platforms. Illustration of server(s) 102 in FIG. 1 is not intended to be limiting. Server(s) 102 may include a plurality of hardware, software, and/or firmware components operating together to provide the functionality attributed herein to server(s) 102. For example, server(s) 102 may be implemented by a cloud of computing platforms operating together as server(s) 102.

Electronic storage 128 may comprise non-transitory storage media that electronically stores information. The electronic storage media of electronic storage 128 may include one or both of system storage that is provided integrally (i.e., substantially non-removable) with server(s) 102 and/or removable storage that is removably connectable to server(s) 102 via, for example, a port (e.g., a USB port, a firewire port, etc.) or a drive (e.g., a disk drive, etc.). Electronic storage 128 may include one or more of optically readable storage media (e.g., optical disks, etc.), magnetically readable storage media (e.g., magnetic tape, magnetic hard drive, floppy drive, etc.), electrical charge-based storage media (e.g., EEPROM, RAM, etc.), solid-state storage media (e.g., flash drive, etc.), and/or other electronically readable storage media. Electronic storage 128 may include one or more virtual storage resources (e.g., cloud storage, a virtual private network, and/or other virtual storage resources). Electronic storage 128 may store software algorithms, information determined by processor(s) 130, information received from server(s) 102, information received from client computing platform(s) 104, and/or other information that enables server(s) 102 to function as described herein.

Processor(s) 130 may be configured to provide information processing capabilities in server(s) 102. As such, processor(s) 130 may include one or more of a digital processor, an analog processor, a digital circuit designed to process information, an analog circuit designed to process information, a state machine, and/or other mechanisms for electronically processing information. Although processor(s) 130 is shown in FIG. 1 as a single entity, this is for illustrative purposes only. In some implementations, processor(s) 130 may include a plurality of processing units. These processing units may be physically located within the same device, or processor(s) 130 may represent processing functionality of a plurality of devices operating in coordination. Processor(s) 130 may be configured to execute components 108, 110, 112, 114, and/or 116, and/or other components. Processor(s) 130 may be configured to execute components 108, 110, 112, 114, and/or 116, and/or other components by software; hardware; firmware; some combination of software, hardware, and/or firmware; and/or other mechanisms for configuring processing capabilities on processor(s) 130. As used herein, the term "component" may refer to any component or set of components that perform the functionality attributed to the component. This may include one or more physical processors during execution of processor readable instructions, the processor readable instructions, circuitry, hardware, storage media, or any other components.

It should be appreciated that although components 108, 110, 112, 114, and/or 116 are illustrated in FIG. 1 as being implemented within a single processing unit, in implementations in which processor(s) 130 includes multiple processing units, one or more of components 108, 110, 112, 114, and/or 116 may be implemented remotely from the other components. The description of the functionality provided by the different components 108, 110, 112, 114, and/or 116 described below is for illustrative purposes, and is not intended to be limiting, as any of components 108, 110, 112, 114, and/or 116 may provide more or less functionality than is described. For example, one or more of components 108, 110, 112, 114, and/or 116 may be eliminated, and some or all of its functionality may be provided by other ones of components 108, 110, 112, 114, and/or 116. As another example, processor(s) 130 may be configured to execute one or more additional components that may perform some or all of the functionality attributed below to one of components 108, 110, 112, 114, and/or 116.

Figure 2:
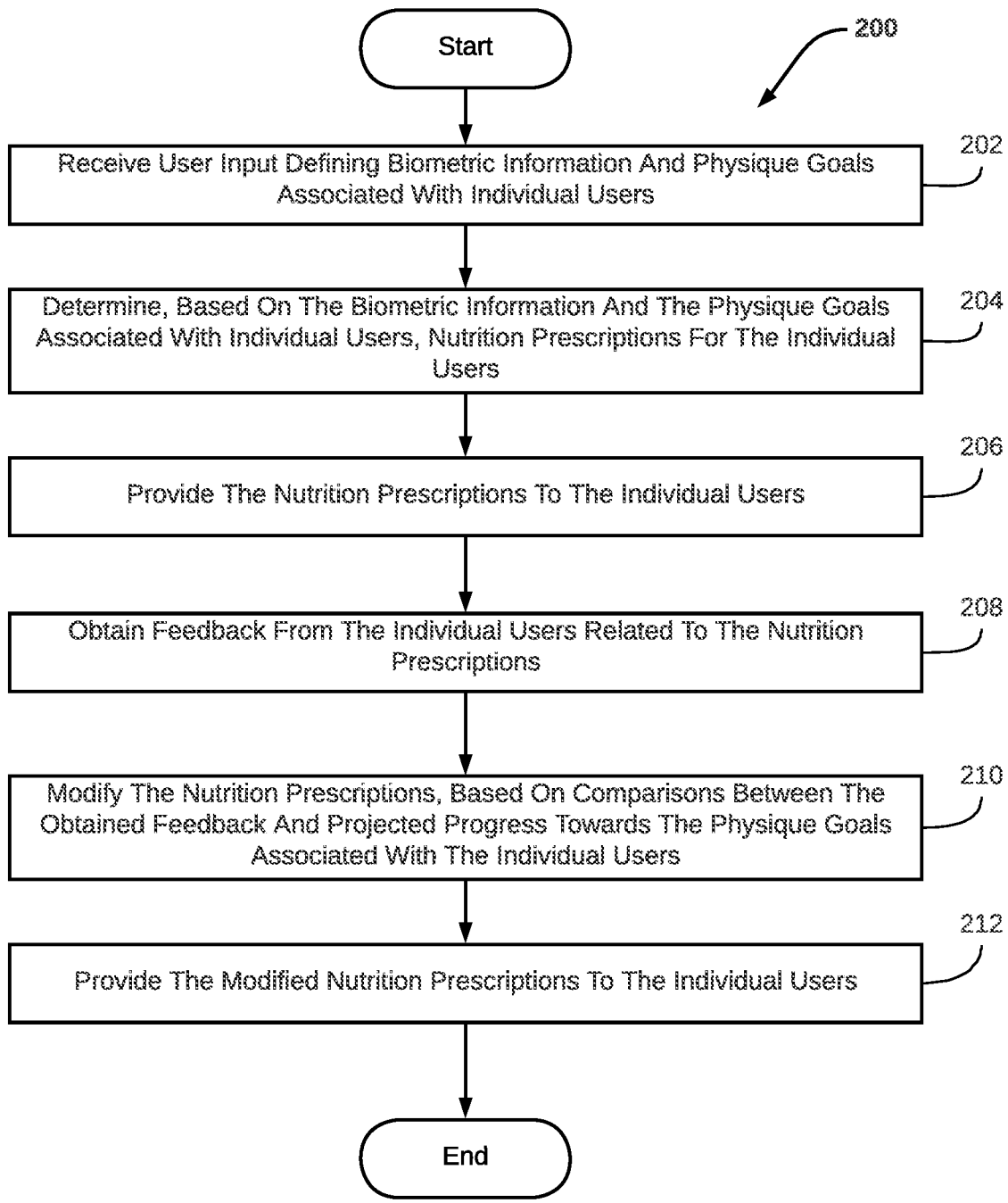
FIG. 2 illustrates a method for generating personalized nutrition prescriptions and modifying the personalized nutrition prescriptions based on feedback, in accordance with one or more implementations.

FIG. 2 illustrates a method 200 for generating personalized nutrition prescriptions and modifying the personalized nutrition prescriptions based on feedback, in accordance with one or more implementations. The operations of method 200 presented below are intended to be illustrative. In some implementations, method 200 may be accomplished with one or more additional operations not described, and/or without one or more of the operations discussed. Additionally, the order in which the operations of method 200 are illustrated in FIG. 2 and described below is not intended to be limiting.

In some implementations, method 200 may be implemented in one or more processing devices (e.g., a digital processor, an analog processor, a digital circuit designed to process information, an analog circuit designed to process information, a state machine, and/or other mechanisms for electronically processing information). The one or more processing devices may include one or more devices executing some or all of the operations of method 200 in response to instructions stored electronically on an electronic storage medium. The one or more processing devices may include one or more devices configured through hardware, firmware, and/or software to be specifically designed for execution of one or more of the operations of method 200.

An operation 202 may include receiving user input defining biometric information, physique goals associated with individual users, and/or other information. The biometric information associated with the individual users may include one or more of age, gender, body fat percentage, body weight, body mass index, level of activity, and/or other information. By way of non-limiting illustration, the received user input may include first user input, and/or other inputs. The first user input may define first biometric information and a first physique goal associated with a first user. Operation 202 may be performed by one or more hardware processors configured by machine-readable instructions including a component that is the same as or similar to input component 108, in accordance with one or more implementations.

An operation 204 may include determining nutrition prescriptions for the individual users. The determination may be based on the biometric information, the physique goals associated with the individual users, and/or other information. The nutrition prescriptions may specify amounts of foods within different macronutrient classifications to be consumed per a consumption period. By way of non-limiting illustration, a first nutrition prescription for the first user may be determined based on the first biometric information, the first physique goal, and/or other information. The first nutrition prescription may specify amounts of foods within different macronutrient classifications to be consumed by the first user per a first consumption period. Operation 204 may be performed by one or more hardware processors configured by machine-readable instructions including a component that is the same as or similar to prescription component 110, in accordance with one or more implementations.

An operation 206 may include providing the nutrition prescriptions to the individual users. The individual users may be intended to consume foods in accordance with the nutrition prescription to facilitate accomplishing the physique goals associated with the individual users. By way of non-limiting illustration, the first nutrition prescription may be provided to the first user. Operation 206 may be performed by one or more hardware processors configured by machine-readable instructions including a component that is the same as or similar to prescription component 110, in accordance with one or more implementations.

An operation 208 may include obtaining feedback from the individual users. The feedback may include one or more of the individual users' body fat percentages, body weights, body mass indexes, and/or other information at or near the time that feedback is obtained. The feedback from the individual users may be compared to projected progress towards the physique goals associated with the individual users. By way of non-limiting illustration, first feedback may be obtained from the first user. The first feedback may be compared to the first user's projected progress towards the first physique goal. Operation 208 may be performed by one or more hardware processors configured by machine-readable instructions including a component that is the same as or similar to feedback component 112, in accordance with one or more implementations.

An operation 210 may include modifying the nutrition prescriptions. The modification may be based on the comparison between the obtained feedback and the projected progress towards the physique goals associated with the individual users. By way of non-limiting illustration, the first nutrition prescription may be modified based on the comparison between first feedback and the projected progress by the first user towards the first physique goal. Operation 210 may be performed by one or more hardware processors configured by machine-readable instructions including a component that is the same as or similar to modification component 114, in accordance with one or more implementations.

An operation 212 may include providing the modified nutrition prescription to the individual users. By way of non-limiting illustration, the modified first nutrition prescription may be provided to the first user. Operation 212 may be performed by one or more hardware processors configured by machine-readable instructions including a component that is the same as or similar to modification component 114, in accordance with one or more implementations.

Although the present technology has been described in detail for the purpose of illustration based on what is currently considered to be the most practical and preferred implementations, it is to be understood that such detail is solely for that purpose and that the technology is not limited to the disclosed implementations, but, on the contrary, is intended to cover modifications and equivalent arrangements that are within the spirit and scope of the appended claims. For example, it is to be understood that the present technology contemplates that, to the extent possible, one or more features of any implementation can be combined with one or more features of any other implementation.

What is claimed:

1. A system configured for generating personalized nutrition prescriptions, the system comprising:
  electronic storage that stores an algorithm for calculating amounts of foods within different macronutrient classifications to consume to achieve physique goals based on biometric information associated with users;
  one or more physical processor configured by machine-readable instructions to:
    receive user input defining biometric information and physique goals associated with individual users, wherein the biometric information associated with the individual users includes one or more of age, gender, body fat percentage, body weight, body mass index, and/or level of activity, wherein the received user input includes first user input defining first biometric information and a first physique goal associated with a first user;
    determine, based on the biometric information and the physique goals associated with the individual users, personalized nutrition prescriptions for the individual users, wherein an individual nutrition prescription is determined for an individual user based on the individual user's associated biometric information and physique goal, wherein determining the nutrition prescriptions includes utilizing the stored algorithm to calculate the amounts of food within different macronutrient classifications for achieving the physique goals based on the biometric information associated with the users, wherein the nutrition prescriptions specify the amounts of foods within different macronutrient classifications to be consumed per a consumption period, wherein a first nutrition prescription for the first user is determined, the determination including using the stored algorithm to calculate first amounts of foods within different macronutrient classifications for achieving the first physique goal based on the first biometric information, the first nutrition prescription specifying the first amounts of foods within different macronutrient classifications to be consumed by the first user per a first consumption period;
    provide the nutrition prescriptions to the individual users, wherein the individual users are intended to consume foods in accordance with the nutrition prescription to facilitate accomplishing the physique goals associated with the individual users, and wherein the first nutrition prescription is provided to the first user.

2. The system of claim 1, wherein the one or more physical processors are further configured by machine-readable instructions to:
  receive user input defining numerical values or levels of intensity corresponding to the physique goals associated with the individual users, wherein individual numerical values are one or more of a value of pounds to lose or gain, a percentage of body fat to lose, and/or a percentage of muscle mass to gain, and wherein individual levels of intensity are one or more of low intensity, moderate intensity, and/or high intensity of achieving the physique goal.

3. The system of claim 1, wherein individual macronutrient classifications include one or more of protein, fat, and/or carbohydrate, and wherein given foods are categorized under one or more of the individual macronutrient classifications.

4. The system of claim 1, wherein the one or more physical processors are further configured to machine-readable instructions to:
  receive user input defining periods of time corresponding to the physique goals associated with the individual users, wherein the physique goals are intended to be accomplished within the corresponding periods of time, wherein received user input includes a first period of time corresponding to the first physique goal, and wherein the first physique goal is intended to be accomplished by the first user within the first period of time.

5. The system of claim 4, wherein the nutrition prescriptions are based on the periods of time corresponding to the physique goals, wherein the first nutrition prescription is determined based on one or more of the first biometric information, the first physique goal, and/or the first period of time.

6. The system of claim 1, wherein the physique goals include one or more of losing body weight, losing body fat, maintaining body weight, and/or gaining muscle mass.

7. The system of claim 1, wherein the one or more physical processors are further configured by machine-readable instructions to:
  obtain feedback from the individual users, wherein feedback includes one or more of the individual users' body fat percentages, body weights, and/or body mass indexes at or near the time that feedback is obtained, wherein feedback from the individual users is compared to projected progress towards the physique goals associated with the individual users, wherein first feedback is obtained from the first user, and wherein the first feedback is compared to the first user's projected progress towards the first physique goal;
  modify the nutrition prescriptions, based on the comparison between the obtained feedback and the projected progress towards the physique goals associated with the individual users, wherein the first nutrition prescription is modified based on the comparison between first feedback and the projected progress by the first user towards the first physique goal; and
  provide the modified nutrition prescriptions to the individual users, wherein the modified first nutrition prescription is provided to the first user.

8. The system of claim 7, wherein the modified nutrition prescriptions are intended to maintain individual users' progress towards the physique goals, wherein the modified first nutrition prescription is intended to maintain the first user accomplishing the first physique goal.

9. The system of claim 7, wherein the nutrition prescriptions, obtained feedback, and the modified nutrition prescriptions are provided as training inputs to train a machine learning model to modify nutrition prescriptions based on obtained feedback.

10. The system of claim 9, wherein the trained machine learning model takes as input a given nutrition prescription and given feedback associated with the given nutrition prescription, and wherein the trained machine learning model is configured to output a modified given nutrition prescription.

11. A method for generating personalized nutrition prescriptions, the method comprising:
  storing an algorithm for calculating amounts of foods within different macronutrient classifications to consume to achieve physique goals based on biometric information associated with users;
  receiving user input defining biometric information and physique goals associated with individual users, wherein the biometric information associated with the individual users includes one or more of age, gender, body fat percentage, body weight, body mass index, and/or level of activity, wherein the received user input includes first user input defining first biometric information and a first physique goal associated with a first user;

determining, based on the biometric information and the physique goals associated with the individual users, personalized nutrition prescriptions for the individual users, wherein an individual nutrition prescription is determined for an individual user based on the individual user's associated biometric information and physique goal, wherein determining the nutrition prescriptions includes utilizing the stored algorithm to calculate the amounts of food within different macronutrient classifications for achieving the physique goals based on the biometric information associated with the users, wherein the nutrition prescriptions specify amounts of foods within different macronutrient classifications to be consumed per a consumption period, including determining a first nutrition prescription for the first user, the determination including using the stored algorithm to calculate first amounts of foods within different macronutrient classifications for achieving the first physique goal based on the first biometric information, the first nutrition prescription specifying the first amounts of foods within different macronutrient classifications to be consumed by the first user per a first consumption period;

providing the nutrition prescriptions to the individual users, wherein the individual users are intended to consume foods in accordance with the nutrition prescription to facilitate accomplishing the physique goals associated with the individual users, including providing the first nutrition prescription to the first user.

12. The method of claim 11, wherein the method further comprises:
receiving user input defining numerical values or levels of intensity corresponding to the physique goals associated with the individual users, wherein individual numerical values are one or more of a value of pounds to lose or gain, a percentage of body fat to lose, and/or a percentage of muscle mass to gain, and wherein individual levels of intensity are one or more of low intensity, moderate intensity, and/or high intensity of achieving the physique goal.

13. The method of claim 11, wherein individual macronutrient classifications include one or more of protein, fat, and/or carbohydrate, and wherein given foods are categorized under one or more of the individual macronutrient classifications.

14. The method of claim 11, wherein the method further comprises:
receiving user input defining periods of time corresponding to the physique goals associated with the individual users, wherein the physique goals are intended to be accomplished within the corresponding periods of time, wherein received user input includes a first period of time corresponding to the first physique goal, and wherein the first physique goal is intended to be accomplished by the first user within the first period of time.

15. The method of claim 14, wherein the nutrition prescriptions are based on the periods of time corresponding to the physique goals, wherein the first nutrition prescription is determined based on one or more of the first biometric information, the first physique goal, and/or the first period of time.

16. The method of claim 11, wherein the physique goals include one or more of losing body weight, losing body fat, maintaining body weight, and/or gaining muscle mass.

17. The method of claim 11, wherein the method further comprises:
obtaining feedback from the individual users, wherein feedback includes one or more of the individual users' body fat percentages, body weights, and/or body mass indexes at or near the time that feedback is obtained, wherein feedback from the individual users is compared to projected progress towards the physique goals associated with the individual users, including obtaining first feedback from the first user, the first feedback being compared to the first user's projected progress towards the first physique goal;

modifying the nutrition prescriptions, based on the comparison between the obtained feedback and the projected progress towards the physique goals associated with the individual users, including modifying the first nutrition prescription based on the comparison between first feedback and the projected progress by the first user towards the first physique goal; and providing the modified nutrition prescriptions to the individual users, including providing the modified first nutrition prescription to the first user.

18. The method of claim 17, wherein the modified nutrition prescriptions are intended to maintain individual users' progress towards the physique goals, wherein the modified first nutrition prescription is intended to maintain the first user accomplishing the first physique goal.

19. The method of claim 17, wherein the nutrition prescriptions, obtained feedback, and the modified nutrition prescriptions are provided as training inputs to train a machine learning model to modify nutrition prescriptions based on obtained feedback.

20. The method of claim 19, wherein the trained machine learning model takes as input a given nutrition prescription and given feedback associated with the given nutrition prescription, and wherein the trained machine learning model is configured to output a modified given nutrition prescription.

* * * * *